(12) United States Patent
Ishiguro et al.

(10) Patent No.: US 6,228,656 B1
(45) Date of Patent: May 8, 2001

(54) METHOD OF CLEAVING SPECIFIC NUCLEIC ACID SEQUENCE

(75) Inventors: Takahiko Ishiguro, Yokohama; Masami Otsuka, Kumamoto; Juichi Saitoh, Yamato; Teruhiko Inoue, Kumamoto; Yukio Sugiura, Kyoto, all of (JP)

(73) Assignee: Tosoh Corporation, Yamaguchi-ken (JP)

( * ) Notice: Subject to any disclaimer, the term of this patent is extended or adjusted under 35 U.S.C. 154(b) by 0 days.

(21) Appl. No.: 09/385,377

(22) Filed: Aug. 30, 1999

(30) Foreign Application Priority Data

Aug. 31, 1998 (JP) .................................................. 10-245453

(51) Int. Cl.⁷ .............................. G01N 33/00; C12Q 1/68; C12P 19/34; C07H 21/02; C07H 21/04
(52) U.S. Cl. ................................ 436/94; 436/800; 435/6; 435/91.1; 536/23.1; 536/24.3; 536/25.3
(58) Field of Search ........................ 435/6, 91.1; 436/94, 436/800; 536/23.1, 24.3, 25.3

(56) References Cited

FOREIGN PATENT DOCUMENTS

| | | |
|---|---|---|
| 0214908A1 | 3/1987 | (EP) . |
| 0714986A1 | 6/1996 | (EP) . |
| WO88/04301 | 6/1988 | (WO) . |
| WO96/40253 | 12/1996 | (WO) . |

OTHER PUBLICATIONS

Ishiguro et al : Nucleic Acids Research, GB Oxford University Press, Surrey vol. 24, No. 24, 1996, pp. 4992–4997, "Fluorescence detection of specific sequence of nucleic acids by Homogenous . . .".

Le Doan et al Antisene Research and Development vol. 1, No. 1, 1991, pp. 43–54 XP000857736Recognition and photo–induced cleavage and cross–linking of nucleic acids by oligonucleotides etc.

Akerman et al Nucleic Acids Research vol. 24, No. 6, 1996, pp. 1080–1090 XP002125717 Single and double stranded photocleavage of DNA by YO, YOYO and TOTO.

Inoue et al Bioorganic and Medicinal Chemistry (Jun. 1999) 7 (6) 1207–11 XP002125718 Flourescence property of oxazole yellow–linked oligonucleotide etc.

*Primary Examiner*—Bradley L. Sisson
(74) *Attorney, Agent, or Firm*—Nixon & Vanderhye PC

(57) ABSTRACT

A method of specifically cleaving a double-stranded DNA (a target nucleic acid) at a specific nucleic acid sequence, which comprises irradiating a solution containing at least the target nucleic acid, a nucleic acid probe (a single-stranded oligonucleotide) linked to an intercalater and spermine with light with an absorption wavelength of the intercalater.

5 Claims, 4 Drawing Sheets

```
                  Triple Helix Site      ↓↓↓  ↓ ↓↓
TH-3:5'-CGATCGTCTCCCTCTCCTTTTAAAGGAGAAAGGGAATCCAGGCCTAG-3'
TH-4:3'-GCTAGCAGAGGGAGAGGAAAATGGATTCCCTTTCTCCTTTCCGGATC-5'
                                          ↑↑
```

METHOD OF CLEAVING SPECIFIC NUCLEIC ACID SEQUENCE

The present invention relates to a method of sequence-specifically cleaving nucleic acids as the gene-constituting substance, and is applicable in the fields of clinical diagnosis, cloning of useful genes and exploration of unknown genes.

It is common to cleave nucleic acids at specific sequences in molecular biology and its applications. For example, when a vector carrying a gene encoding a desired protein is constructed for production of the desired protein in microorganisms such as *Escherichia coli*, human cells or other animal cells, it is necessary to cleave a nucleic acid as the gene at a specific sequence with a restriction enzyme.

For such sequence-specific cleavage of nucleic acids, restriction enzymes, which recognize base sequences in nucleic acids and cleave inter-nucleotide linkages, are commonly used, and hundreds of restriction enzymes have already been known.

When restriction enzymes are used, it is necessary to select a restriction enzyme which recognizes a specific sequence to cleave. However, even hundreds of known restriction enzymes are not enough to cleave nucleic acids at any sequences. For example, a promising cancer treatment by specific cleavage of a target cancer gene with the aim of hindering the development of the cancer gene requires a restriction enzyme which specifically cleaves a specific sequence in the cancer gene to be cleaved to attain the aim, but it is possible that there is no restriction enzyme that recognizes and cleaves the specific sequence.

Accordingly, the object of the present invention is to provide a method of specifically cleaving a specific nucleic acid sequence in a double-stranded DNA (hereinafter referred to as a target nucleic acid) which enables cleavage of a specific nucleic acid sequence without using a restriction enzyme.

In order to achieve the above-mentioned object, the present invention provides a method of specifically cleaving a double-stranded DNA (a target nucleic acid) at a specific nucleic acid sequence, which comprises irradiating a solution containing at least the target nucleic acid, a nucleic acid probe (a single-stranded oligonucleotide) linked to an intercalater and spermine with light of an absorption wavelength of the intercalater.

Figures 5, 6:
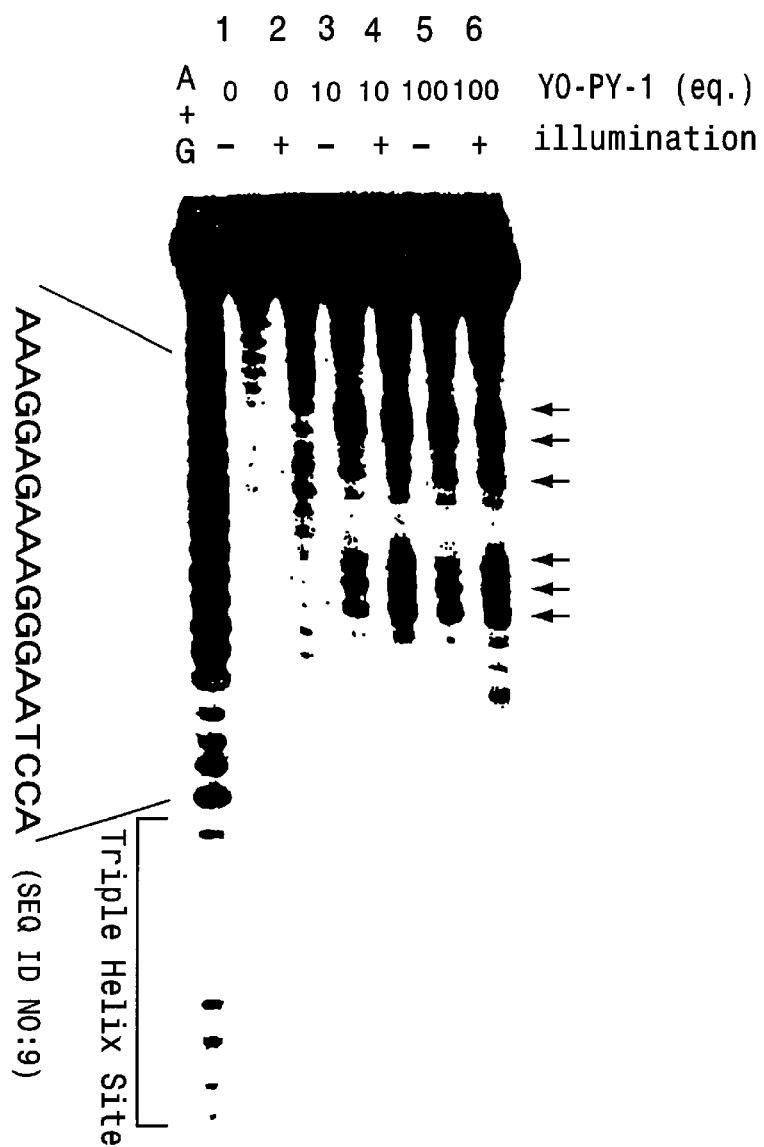
FIG. 5 shows a cleavage pattern of labeled TH-3 obtained by electrophoresis of the double-stranded DNA formed by TH-3 and TH-4 after cleavage by YO-PY-1.

In FIG. 6, the arrows indicate the cleavage sites by YO-PY-1 in the double stranded DNA formed by TH-3 and TH4.

Now, the present invention will be described in detail.

It is possible to design a nucleic acid probe (a single-stranded DNA) which binds to a specific nucleic acid sequence in a double-stranded DNA to form a triple-strand, and the rules of base selection for the designing are already known well (Takashi Ito, Protein, Nucleic Acid and Enzyme, Vol. 38, No. 3, pp.541–550, 1993). On the other hand, the present applicant reported a fluorescent intercalative dye-linked probe obtained by linking a fluorescent intercalative dye to a single-stranded oligonucleotide having a nucleic acid sequence specifically hybridizable with a specific sequence in a single-stranded target nucleic acid so that the fluorescent dye intercalates into the double strand formed by hybridization of the specific nucleic acid sequence and changes its fluorescent characteristic (Japanese Patent Application JP7-185599, EP-A-714986, Nucleic Acid Research, 24(24), pp.4992–4997, 1996). Herein, the hybrid of the intercalater-linked nucleic acid probe and the target nucleic acid is sometimes referred to as a cleavage probe, and the single-stranded oligonucleotide in the cleavage probe is sometimes referred to simply as a nucleic acid probe.

As a result of their extensive research with a view to achieving the above-mentioned object, the present inventors have recently found that when a target nucleic acid is irradiated with light with a specific wavelength in the presence of spermine after addition of an intercalater-linked nucleic acid probe having a nucleic acid sequence specifically hybridizable with a specific nucleic acid sequence in the double-stranded DNA as a cleavage probe, the intercalater intercalates into the target nucleic acid and absorbs the light of the specific wavelength to cleave the target nucleic acid where the cleavage probe binds, namely at the specific nucleic acid sequence.

In the present invention, any substance that intercalates into a double-stranded DNA may be used as the intercalater without any particular restriction. For example, fluorescent intercalative dyes such as thiazole orange and oxazole yellow may be mentioned. The intercalater can be covalently linked to the nucleic acid probe, optionally via a linker of an appropriate length. Although any linker molecule that does not hinder the intercalater from intercalating into the target nucleic acid may be used without any particular restriction, a particularly preferable linker is a bifunctional hydrocarbon having functional groups at both ends for easiness of linkage between the two. Alternatively, a commercial reagent (C6-Thimolmodifier, Clontech) may be used.

The intercalater may be linked to any sites of the nucleic acid probe, including the 5' end, the 3' end and the middle of the nucleic acid probe without any particular restriction, as long as the linkage neither hinders the cleavage probe from binding to the specific nucleic acid sequence in the target nucleic acid nor hinders the linked intercalater from intercalating into the target nucleic acid.

According to the present invention, the target nucleic acid is cleaved at the site to which the cleavage probe specifically binds, namely at the specific nucleic acid sequence. Thus, the length of the linker and the location of the linked intercalater in the cleavage probe are crucial for control of the cleavage site in the target nucleic acid. Namely, for example, when the cleavage probe has an intercalater at the end, the target nucleic acid is cleaved several bases to tens of bases away from the end of the specific nucleic acid sequence in the target nucleic acid, depending on the length of the linker.

The nucleic acid probe as a constituent of the cleavage probe is preferably a single-stranded oligonucleotide of 6 to 100 nucleotides long, preferably 10 to 30 nucleotides long, to secure the specificity for the specific nucleic acid sequence in the target nucleic acid. The specific nucleic acid sequence in the target nucleic acid is a base sequence containing the site in the target nucleic acid to be cleaved by the method of the present invention and can be determined arbitrarily. For example, when a double-stranded nucleic acid not to be cleaved coexists with the target nucleic acid to be cleaved, it is preferred to select a base sequence peculiar to the target nucleic acid (in other words, absent in the other nucleic acid) as the specific nucleic acid sequence. As to the base sequence of the nucleic acid probe, selection of T, and C or 5-methylcytosine, as the bases assigned to A-T pairs, and G-C pairs, respectively, in the target nucleic acid (double-stranded DNA) permits formation of a stable triple strand of the Pyr-Pur-Pyr type.

The target nucleic acid is cleaved at the specific nucleic acid sequence when irradiated with light of a specific wavelength after addition of the cleavage probe in the presence of spermine. As to the amount of the cleavage probe coexisting with the target nucleic acid, though the cleavage probe works well when the amount of the cleavage probe is much the same as the estimated amount of the target nucleic acid, the target nucleic acid is cleaved efficiently when 10 to 100 times as much of the cleavage probe is used. The amount (final concentration) of spermine to be used is about 0.1 mM to 1.0 mM, preferably about 0.5 mM.

The irradiation light is not particularly restricted so long as it contains a ray of the specific absorption wavelength of the intercalater. For example, when the intercalater is oxazole yellow, light of 490 nm may be mentioned as the light of the specific wavelength.

Now, the present invention will be described in further detail by referring to Examples. However, it should be understood that the present invention is by no means restricted to these specific Examples.

EXAMPLE 1

Preparation of Oligonuleotides

Oligonucleotides DS-1, TH-1, Th-2, TH-3 and Th-4 were prepared by a commercial DNA synthesizer. The base sequences of the respective oligonucleotides are shown below.
DS-1(SEQ ID NO: 1): 5'-TTTTCCTCTCCCTCT-3'
TH-1(SEQ ID NO: 2): 5'-GATCGGCAGGGGAATCT CCCTCTCCTTTTATGGGC-3'
TH-2(SEQ ID NO: 3): 5'-TCGAGCCCATAAAAGG AGAGGGAGATTCCCCTGCC-3'
TH-3(SEQ ID NO: 4): 5'-CGATCGTCTCCCTCTCC TTTTACCTAAGGGAAAGAGGAAAGGCCTAG-3'
TH-4(SEQ ID NO: 5): 5'-CTAGGCCTTTCCTCTTT CCCTTAGGTAAAAGGAGAGGGAGAGGATCG-3'

Thiol-modified oligonucleotides PU-1 and PY-1 (nucleic acid probes) were prepared by a DNA synthesizer by using a commercial reagent (C6-ThiolModifier, trade name, Clontech) by a conventional method. The trityl group attributable to the commercial reagent (C6-ThiolModifier) was eliminated by a conventional method. The base sequences of PU-1 and PY-1 are shown below.

The base sequences of the respective oligonucleic acids are shown below (* indicates 5-methylcytosine).
PU-1(SEQ ID NO: 6): 5'-HS (CH$_2$)$_6$-OPO$_3$-AGAGGGAGAGGAAAA-3'
PY-1(SEQ ID NO: 7): 5'-HS(CH$_2$)$_6$-OPO$_3$-TTTTC*C*TC*TC*C*C*TC*T-3'

EXAMPLE 2

Preparation of Cleavage Nucleic Acid Probes

PU-1 prepared in Example 1 was purified by high-speed liquid chromatography by a conventional method. Dithiothreitol (10 μM, 20 μL) was added to the fraction containing PU-1 to give solution A. Oxazole yellow (YO(CH$_2$)$_3$I) prepared as disclosed in the literature (Japanese Patent Application JP7-185599, EP-A-713986, Nucleic Acids Research, 24(24), pp.4992–4997, 1996) was added to a liquid mixture of DMA (200 μl), 1.0 M phosphate buffer (pH 10.0, 300 μl) and water (500 μl) was mixed with to saturation to give solution B.

Solution A and solution B were mixed in a ratio of 3:1, allowed to react in the presence of argon for 2 hours and subjected to liquid chromatography through a gel filtration column (Sephadex G-25, Pharmacia) using TEAA buffer pH 7.0 containing 5% acetonitrile as the eluent for purification.

The YO-PY-1 isolated in fractions was concentrated, dissolved in distilled water and purified again by high speed liquid chromatography in a conventional manner, and the YO-PU-1 in fractions was evaporated to dryness under reduced pressure. The concentration of YO-PU-1 was determined from the absorbance at 260 nm.

Figure 1:
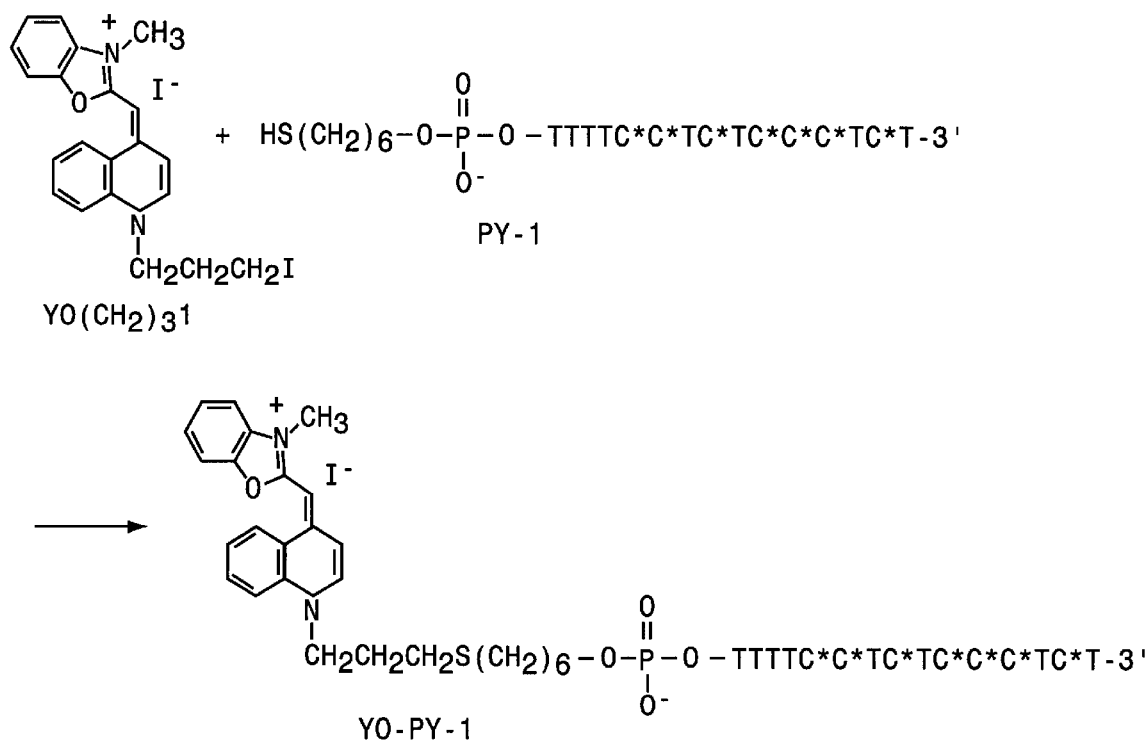
FIG. 1 is a scheme explaining preparation of YO-PY-1.

PY-1 prepared in Example 1 was also subjected to a similar procedure to give YO-PY-1. The base sequences of the respective nucleic acid probes are shown below (* indicates 5-methylcytosine). FIG. 1 is a scheme showing the preparation of these cleavage nucleic acid probes (intercalater-linked nucleic acid probes).
YO-PU-1:    5'-YO-(CH$_2$)$_3$-S(CH$_2$)$_6$-OPO$_3$-AGAGGGAGAGGAAAA-3'
YO-PY-1:    5'-YO-(CH$_2$)$_3$-S(CH$_2$)$_6$-OP0$_3$-TTTTC*C*TC*TC*C*C*TC*T-3'

EXAMPLE 3

Formation of a Double Strand and Fluorescence Measurement

DS-1 prepared in Example 1 was added to Tris-HCl buffer (20 mM, pH 7.5, 50 μl) containing YO-PU-1 (30 pmol), and the resulting liquid mixture was heated to 90° C. for annealing and allowed to cool to room temperature. Then, the same Tris-HCl buffer (500 ml) as mentioned above was further added, and the fluorescence was measured at an excitation wavelength of 490 nm and an emission wavelength of 510 nm. The results are shown in FIG. 2.

Figure 2:
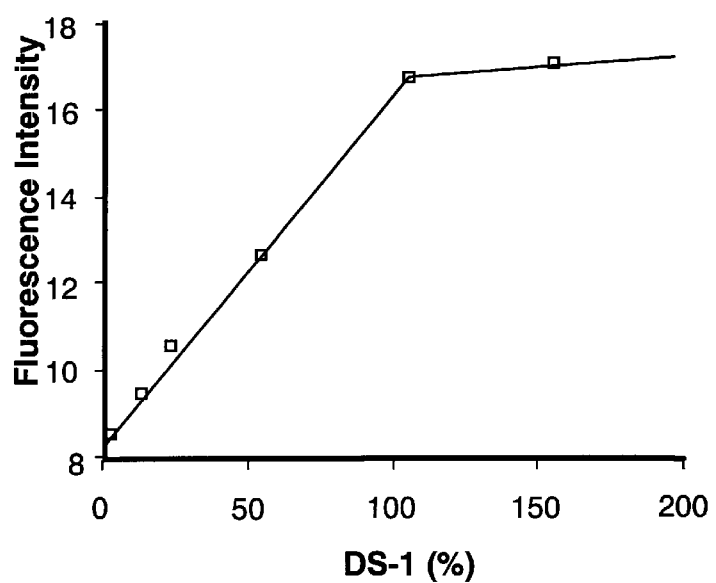
FIG. 2 shows fluorescence enhancement of YO-PU-1 upon formation of a double strand with a complementary strand DS-1.

FIG. 2 indicates specific binding of the cleavage probe to DS-1.

EXAMPLE 4

Formation of a Triple Strand and Fluorescence Measurement

TH-1 and TH-2 prepared in Example 1 were added to Tris-HCl buffer (20 mM, pH 7.5, 50 μl), and the resulting liquid mixture was heated to 90° C. for annealing and allowed to cool to room temperature to form a double-stranded DNA (a target nucleic acid). The resulting target nucleic acid and YO-PY-1 were added to Tris-acetate buffer (25 mM, pH 5.1, 100 μl) containing NaCl (50 mM), MgCl$_2$ (20 mM) and spermine (0.5 mM) and incubated at 25° C. for 30 minutes. Then, the same Tris-HCl buffer as mentioned above (500 μml) was added, and the fluorescence was measured at an excitation wavelength of 490 nm and an emission wavelength of 510 nm. For comparison, the same procedure was done with spermine-free buffer. The results are shown in FIG. 3.

Figure 3A:
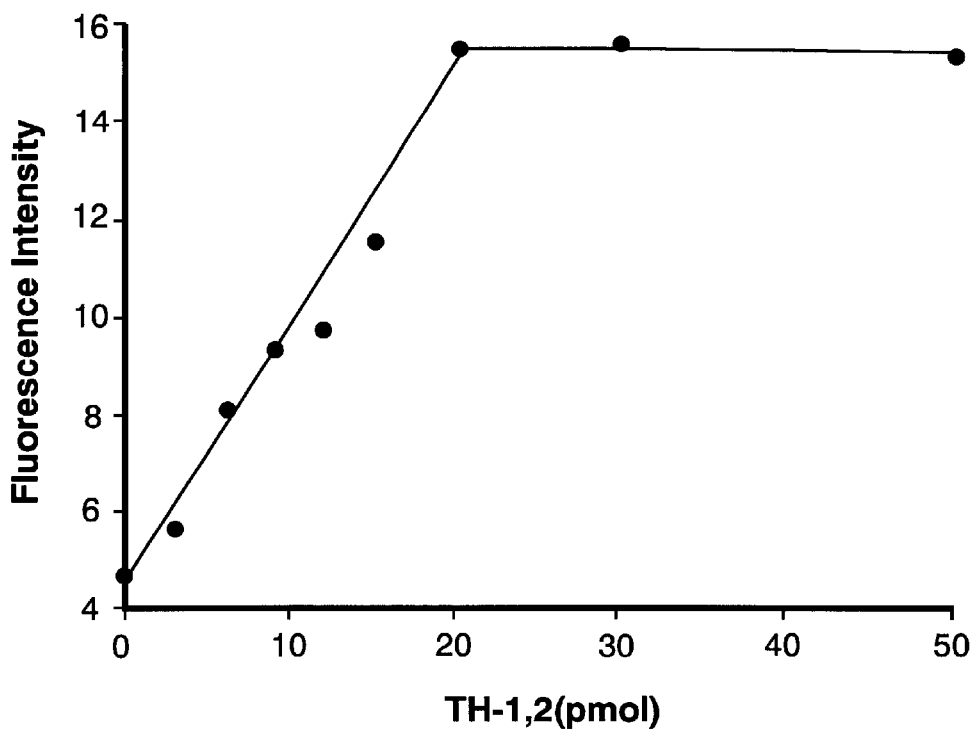
FIG. 3 shows fluorescence enhancement of YO-PY-1 upon formation of a triple strand with a double strand formed by TH-1 and TH-2 in the presence of spermine (A) and in the absence of spermine (B).
Figure 3B:
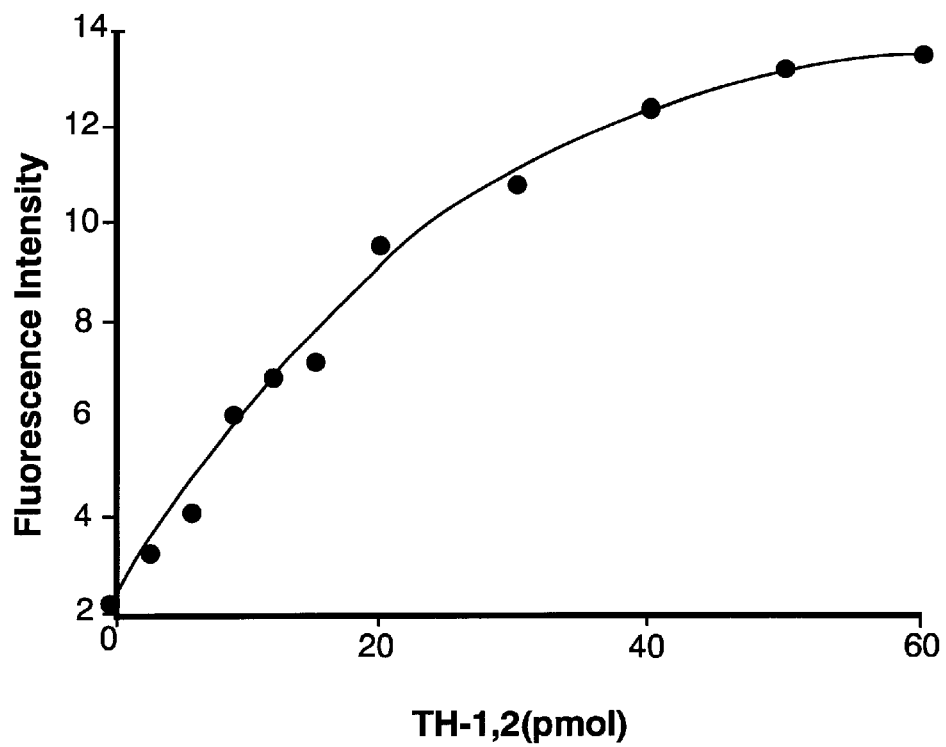

It is evident from FIG. 3 that the cleavage probe specifically formed a triple strand with the target nucleic acid, and that the presence of spermine was effective in its formation.

It was also confirmed that the fluorescent intercalative dye as the intercalater in the cleavage probe enhanced the fluorescence upon formation of the triple strand.

EXAMPLE 5

Cleavage of Target Nucleic Acid

The 5' end of either TH-3 or TH-4 prepared in Example 1 was labeled by using T4 polynucleotide kinase and [γ-32P]-ATP (32P-labeled ATP). The labeled strand was mixed with the unlabeled complementary strand, and the mixture was heated to 90° C. for annealing and then allowed to cool to room temperature to form a double-stranded DNA (a target nucleic acid).

The resulting target nucleic acid (4 mM, containing about 100K cpm of the labeled strand) was added to Tris-HCl buffer (50 mM, pH 5.8, 1 ml) containing NaCl (50 mM), $MgCl_2$ (20 mM), spermine (0.5 mM) and 10 equivalents or 100 equivalents of YO-PY-1, then incubated at 20° C. for 30 minutes and irradiated with visible light at the same temperature.

Figure 4:
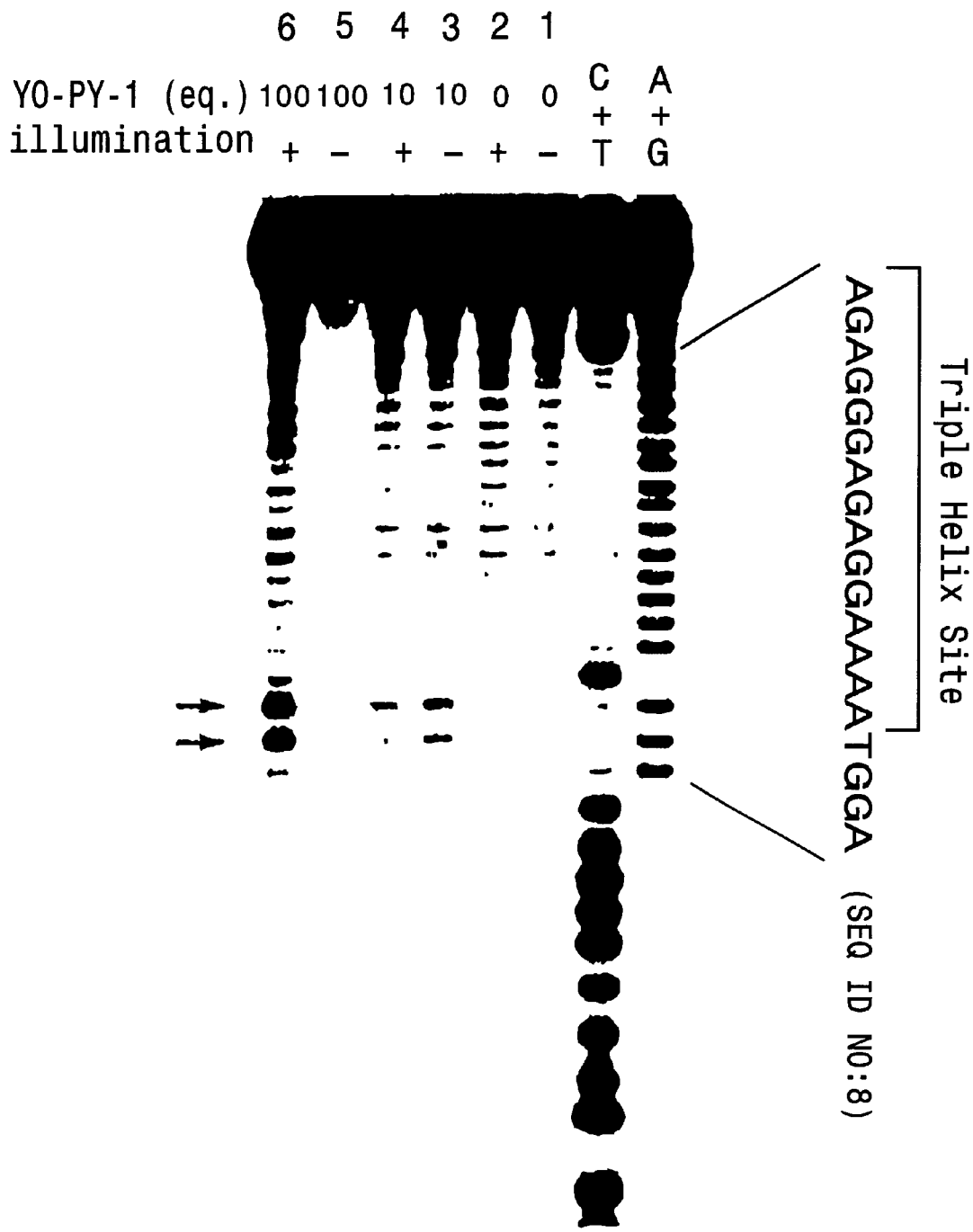
FIG. 4 shows a cleavage pattern of labeled TH-4 obtained by electrophoresis of the double-stranded DNA formed by TH-3 and TH-4 after cleavage by YO-PY-1.

The DNA was precipitated from the liquid mixture by addition of ethanol and dried under reduced pressure. A portion of the sample containing 20K cpm of the labeled strand was subjected to electrophoresis on 12% denatured polyacrylamide gel at 2000V for 3 hours and then autoradiography on an X-ray film. The results are shown in FIGS. 4 to 6.

The arrows in the figures indicate the locations of the cleavage sites in the target nucleic acid. It can be seen that the cleavage probe cleaved the target nucleic acid site-specifically, and that the target nucleic acid can be cleaved at an arbitrary site (specific nucleic acid sequence) through selection of the base sequence of the nucleic acid probe.

As is evident from the above description, the present invention provides a method of specifically cleaving a double-stranded DNA at a specific nucleic acid sequence (an arbitrary sequence). For its applicability to sequences which can not be dealt with by the conventional cleaving method using restriction enzymes, the method is useful not only in such fields as cloning of useful genes and exploration of unknown genes but also in promising fields such as gene diagnosis and gene therapy.

In particular, according to the present invention, because the target double-stranded DNA can be cleaved merely by addition of the cleavage probe to a sample and subsequent irradiation with light of a specific wavelength in the presence of spermine for about 1 hour, it is possible to meet the general demand for speed and simplicity, and because it involves no skilled operations, there is no possibility that different results are obtained by different operators. In addition, in the present invention, because DNA double strands are not cleaved until irradiation with light of a specific wavelength, it is possible to arbitrarily select the timing of cleavage even if the target nucleic acid coexists with the cleavage probe. For example, when light irradiation follows confirmation of migration of the cleavage probe to cells containing the target nucleic acid, it is possible to effectively cleave the target nucleic acid, and its use for gene therapy is expected. Further, because it is possible to arbitrarily select the timing of cleavage, the method can be so designed as to avoid damage to double-stranded DNA having a specific nucleic acid sequence or a similar sequence which is not to be cleaved.

Because the intercalater-linked nucleic acid probe used as the cleavage probe in the present invention has a characteristic that the intercalater enhances the fluorescence intensity upon hybridization of the probe with the target nucleic acid, for example, it is possible to introduce the cleavage probe to cells in a tissue containing the target nucleic acid and then irradiate the cleavage probe with light of a specific wavelength preferable for the cleavage in the present invention after confirmation of binding of the cleavage probe to the target nucleic acid, based on the fluorescence from the cells.

What is claimed is:

1. A method of specifically cleaving a double-stranded DNA (a target nucleic acid) at a specific nucleic acid sequence, which comprises irradiating a solution containing at least the target nucleic acid, a nucleic acid probe (a single-stranded oligonucleotide) in the form of a triple strand, said nucleic acid probe being linked to an intercalater, and spermine with light with an absorption wavelength of the intercalater to cleave the target nucleic acid.

2. The method according to claim 1, wherein the intercalater is a fluorescent intercalative dye.

3. A method of specifically cleaving a double-stranded DNA, in the absence of a restriction enzyme, at a specific nucleic acid sequence of said double stranded DNA, said method comprising the steps of:

forming a triple stranded DNA complex comprising said double-stranded DNA and a nucleic acid probe which hybridizes to said double-stranded DNA, said probe being linked to an intercalater which intercalates in said double-stranded DNA;

contacting said triple-stranded DNA with spermine and light of a wavelength which is absorbed by said intercalater and causes specific cleavage of said double-stranded DNA at said specific nucleic acid sequence.

4. The method of claim 3 wherein said dye is a fluorescent dye.

5. The method of claim 4 wherein said dye is cell permeable.

* * * * *

SEQUENCE LISTING

```
<160> NUMBER OF SEQ ID NOS: 9

<210> SEQ ID NO 1
<211> LENGTH: 15
<212> TYPE: DNA
<213> ORGANISM: Artificial Sequence
<220> FEATURE:
<223> OTHER INFORMATION: Description of Artificial Sequence:
      synthetic oligonucleotide

<400> SEQUENCE: 1
ttttcctctc cctct                                                    15

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence:
      synthetic oligonucleotide

<400> SEQUENCE: 2
gatcggcagg ggaatctccc tctccttta tgggc                               35
```

```
<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence:
      synthetic oligonucleotide

<400> SEQUENCE: 3
tcgagcccat aaaaggagag ggagattccc ctgcc                         35

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence:
      synthetic oligonucleotide

<400> SEQUENCE: 4
cgatcgtctc cctctccttt tacctaaggg aaagaggaaa ggcctag            47

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence:
      synthetic oligonucleotide

<400> SEQUENCE: 5
ctaggccttt cctctttccc ttaggtaaaa ggagagggag aggatcg            47

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: nucleic
      acid probe

<400> SEQUENCE: 6
agagggagag gaaaa                                               15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: nucleic
      acid probe

<400> SEQUENCE: 7
ttttcctctc cctct                                               15

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 8
agagggagag gaaaatgga                                           19
```

```
<210> SEQ ID NO 9
<211> LENGTH: 19
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 9
aaaggagaaa gggaatcca                                              19
```